US006875446B2

(12) United States Patent
Forsman et al.

(10) Patent No.: US 6,875,446 B2
(45) Date of Patent: Apr. 5, 2005

(54) METHOD FOR PROPHYLAXIS AND/OR TREATMENT OF THROMBOEMBOLISM

(75) Inventors: Sigbrit Forsman, Lerum (SE); Christer Karlsson, Lindome (SE); Magnus Karlsson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/347,968

(22) Filed: Jan. 21, 2003

(65) Prior Publication Data

US 2003/0118644 A1 Jun. 26, 2003

Related U.S. Application Data

(63) Continuation of application No. 09/424,740, filed as application No. PCT/SE99/01471 on Aug. 27, 1999, now Pat. No. 6,521,253.

(30) Foreign Application Priority Data

Sep. 3, 1998 (SE) ................................. 9802973

(51) Int. Cl.$^7$ ............................. A61K 9/20; A61K 9/22; A61K 9/14
(52) U.S. Cl. ........................ 424/464; 424/468; 424/484; 424/488; 424/489
(58) Field of Search ................................ 424/464, 468, 424/484, 488, 489

(56) References Cited

U.S. PATENT DOCUMENTS

| | | | | |
|---|---|---|---|---|
| 5,430,023 | A |   | 7/1995 | Gesellchen et al. ........... 514/18 |
| 5,510,369 | A | * | 4/1996 | Lumma et al. .............. 514/422 |
| 5,532,267 | A |   | 7/1996 | Nakayama .................. 514/467 |
| 5,714,485 | A |   | 2/1998 | Lumma et al. .............. 514/247 |
| 5,798,377 | A | * | 8/1998 | Lumma et al. .............. 514/423 |
| 5,840,769 | A | * | 11/1998 | Kolter et al. ................ 514/781 |

FOREIGN PATENT DOCUMENTS

| | | |
|---|---|---|
| CA | 2239931 | 1/2000 |
| EP | 0255002 | 2/1988 |
| EP | 0643073 | 3/1995 |
| EP | 0803251 | 10/1997 |
| EP | 1044680 | 10/2000 |
| WO | 9305069 | 3/1993 |
| WO | 9311152 | 6/1993 |
| WO | 9429330 | 12/1994 |
| WO | 9601622 | 1/1996 |
| WO | 9717947 | 5/1997 |
| WO | 9722340 | 6/1997 |
| WO | 9723499 | 7/1997 |
| WO | 9813029 | 4/1998 |
| WO | 9961002 | 12/1999 |
| WO | 0001368 | 1/2000 |
| WO | 0009090 | 2/2000 |
| WO | 0018447 | 4/2000 |
| WO | 0059479 | 10/2000 |
| WO | 0059481 | 10/2000 |

OTHER PUBLICATIONS

Lachman, L. et al. The Theory and Practice of Industrial Pharmacy. Lca & Febiger Publ.,$3^{rd}$ Ed.pp. 343–345, 1986.
Sandell, E. Galenic Pharmaceuticals, $2^{nd}$ Ed. Stockholm, Sweden, pp. 288–290, 1967.
Composition of Seloken metoprolol tartrate tablets, manufactured by Hässle and approved in Sweden in 1975.
Composition of felodipine immediate–release tablets, manufactured by Hässle and registered in Australia in 1987.
Composition of Seloken metoprolol tartrate tablets, manufactured by Hässle and registered in Sweeden in 1975.

* cited by examiner

Primary Examiner—Thurman K. Page
Assistant Examiner—Blessing Fubara
(74) Attorney, Agent, or Firm—White & Case LLP

(57) ABSTRACT

A new oral IR formulation in solid form for a low molecular weight thrombin inhibitor having pH dependant dissolution, characterized in that the formulation comprises a filler or a combination of fillers having disintegrant properties in an amount higher than 35% w/w of the formulation.

28 Claims, 2 Drawing Sheets

Example 1

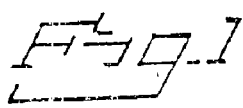
Example 1
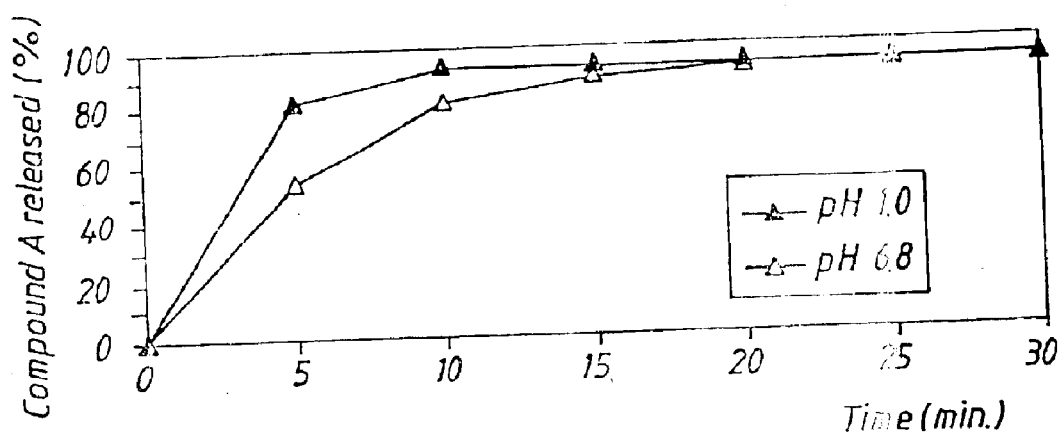

Example 2
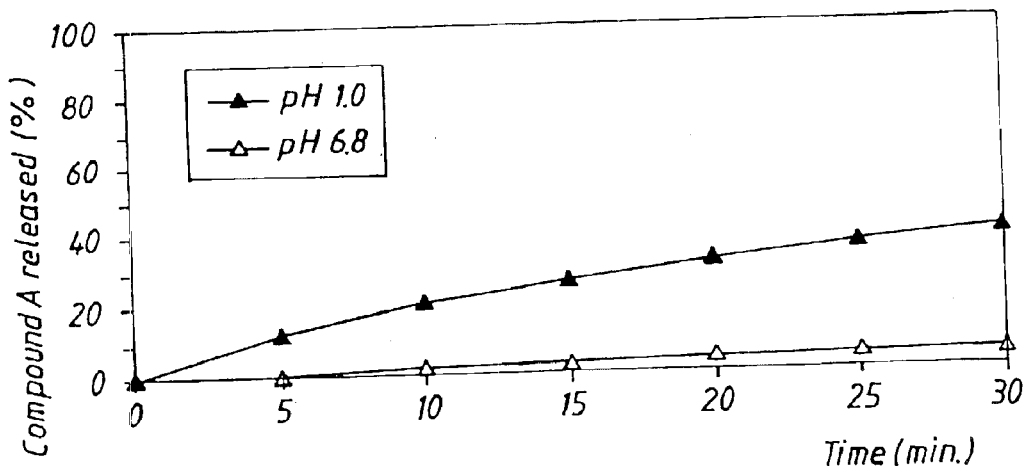
Exampel 3
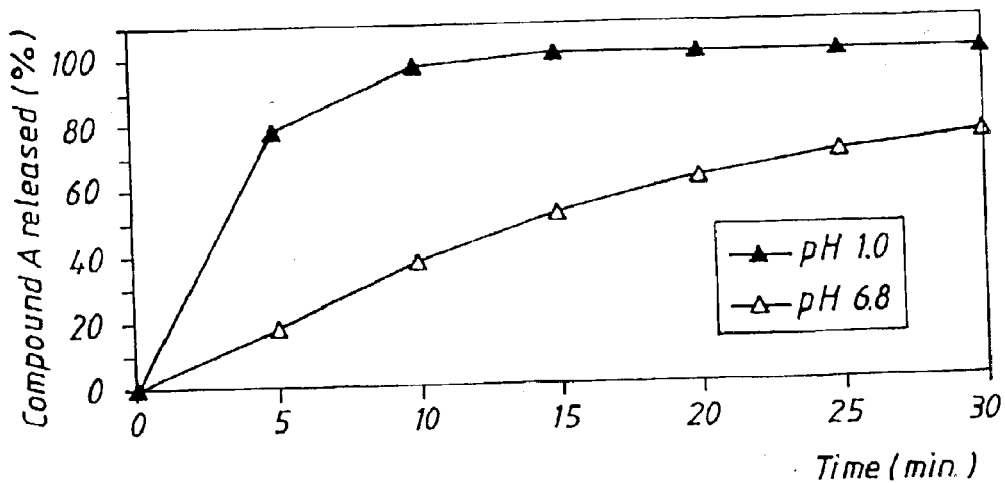

METHOD FOR PROPHYLAXIS AND/OR TREATMENT OF THROMBOEMBOLISM

This application is a continuation of U.S. patent application Ser. No. 09/424,740, filed Nov. 30, 1999, now U.S. Pat. No. 6,521,253 which is a §371 of international patent application PCT/SE99/01471, filed Aug. 27, 1999.

FIELD OF THE INVENTION

The invention relates to a solid dosage form of a low molecular weight thrombin inhibitor formulated as immediate release (IR) tablets as well as a process for manufacture thereof. The invention also relates to the medical use of the formulation in the prophylaxis and/or treatment of thromboembolism.

BACKGROUND OF THE INVENTION

The thrombin inhibitor, used in the formulation of the present invention is a low molecular weight drug with pH dependent solubility. It is characterised by a low solubility at basic pH which is dramatically increased in the protonated form at acidic pH. Thus, upon administration in conventional IR formulations, fast dissolution of the drug is obtained in acidic pH while markedly slower dissolution is obtained at more neutral pH. This variability in dissolution is not acceptable for safe, efficient and convenient therapy. The present invention provides an immediate release formulation based on conventional manufacturing processes with careful chosen excipients that provides a dissolution which is not, or very little dependent on pH.

Several different ways have been suggested in order to prepare immediate-release solid dosage forms.

Lachman (The theory and practice of industrial pharmacy 1986, 343, appA) describes the composition and manufacturing of two different standard granulates for IR tablets. These two compositions gave very poor quality of the granulates, which gave unacceptable tablets with very low hardness. These compositions do not work with the low molecular weight thrombin inhibitors used in connection with the present invention. The tablets do not answer to the definition of a rapidly dissolving drug product presented in Guidance for Industry. Waiver of in Vivo Bioavailability and Bioequivalens Studies for Immediate Release Solids Dosage Forms Containing Certain Active Moieties/Active Ingredients Based on Biopharnaceutics Classification System. Tablets must release 85% or more of stated amount within 30 min.

DESCRIPTION OF THE INVENTION

It has now been found that low molecular weight peptide-based thrombin inhibitors with pH-dependent solubility—including their salts—can be formulated as IR tablets with no or very little pH dependent dissolution.

Therefore, the object of the present invention is to provide a novel pharmaceutical formulation comprising a low molecular weight peptide-based thrombin inhibitor formulated as an IR-tablet with no or very little pH dependent dissolution and a process for the preparation of such formulation.

Thrombin inhibitors referred to in this application are low molecular weight peptide-based thrombin inhibitors with pH dependent solubility. The term "low molecular weight peptide-based thrombin inhibitors" will be well understood by one skilled in the art to include thrombin inhibitors with one to four peptide linkages, and/or with a molecular weight below 1000, and includes those described generically and, more preferably, specifically in the review paper by Claesson in Blood Coagul. Fibrin. (1994) 5, 411, as well as those disclosed in U.S. Pat. No. 4,346,078; International Patent Applications WO 97/23499, WO 97/02284, WO 97/46577, WO 98/01422, WO 93/05069, WO93/11152, WO 95/23609, WO95/35309, WO 96/25426, WO 94/29336, WO WO 93/18060 and WO 95/01168; and European Patent Applications 623 596, 648 780,468 231, 559 046, 641 779, 185 390, 526 877, 542 525, 195 212, 362 002, 364 344, 530 167, 293 881, 686 642, 669 317 and 601 459.

Preferred low molecular weight peptide-based thrombin inhibitors include those known collectively as the "gatrans". Particular gatrans which may be mentioned include HOOC—$CH_2$(R)Cha-Pic-Nag-H (known as inogatran; see International Patent Application WO 93/11152 and the list of abbreviations therein) and HOOC—$CH_2$—(R)Cgl-Aze-Pab-H (known as melagatran; see International Patent Application WO 94/29336 and the list of abbreviations therein).

The preferred low molecular weight peptide-based thrombin inhibitor is selected from the group consisting of inogatran, (Glycine, N-[2-[2-[[[3-[(aminoimino-methyl)amino]propyl]amino]carbonyl]-1-piperidinyl]-1-(cyclohexylmethyl)-2-oxoethyl]-, [2R-[2S]]-), melagatran, (Glycine, N-[2-[2-[[[[4 (aminoiminomethyl)phenyl]methyl]amino]carbonyl]-1-azetidinyl]-1-cyclohexyl-2-oxoethyl]-, [2R-[2S]]-) and compound A, (Glycine, N-[1-cyclohexyl-2-[2-[[[[4-[(hydroxyimino)aminomethyl]phenyl]methyl]amino]carbonyl]-1-azetidinyl]-2-oxoethyl]-, ethyl ester, [S-(R*, S*)]-).

The particularly preferred low molecular weight thrombin inhibitor Compound A is effective for the treatment of thromboembolism. Compound A is described in the International Patent Application WO 97/23499. Compound A is a low molecular weight thrombin inhibitor with good oral bioavalability, low variability and limited food interaction. No solid dosage forms containing this thrombin inhibitor have been reported.

In order to produce tablets which provides a dissolution which is not or very little dependent on pH, compound A should have a particle size less than 300 µm, preferably less than 150 µm and with a preferred mean particle size less than 80 µm. With other low molecular weight thrombin inhibitor with low solubility at basic pH and pH dependent solubility the requirements on the particle size will depend on the level of low solubility.

It has been found that by carefully selecting excipients the pH dependent dissolution could be reduced and giving a tablet release of more than 85% within 30 minutes in acidic as well as neutral environments. This in spite of Compound A having an extremely pH dependent solubility.

The formulation according to the invention comprises the thrombin inhibitor, a filler or a combination of fillers, said filler/fillers having disintegrant properties (due to swelling) and, optionally, non swelling filler(s) disintegrant(s), binder(s) and/or lubricant(s).

The amount of filler/fillers having disintegrant properties constitutes more than 35% (w/w), preferably more than 50% (w/w) of the formulation.

Some excipients can serve multiple purposes, e.g. be a filler and a disintegrant at the same time. An excipient used in higher amounts than 35% is in the invention defined as a filler but may contribute with other important properties for the formulation e.g. disintegration, binding or lubrication.

The filler with disintegrant properties is selected from the group consisting of cellulose per se (such as microcrystalline cellulose, microfine cellulose) starch per se (such as maize starch, sodium starch glycollate, potato starch, rice starch, wheat starch).

The nonswelling filler is selected from the group sugars (such as mannitol, sorbitol, dextrose, xylitol, sucrose, laktos).

The disintegrant is selected from the group consisting of cellulose per se (such as microcrystalline cellulose, microfine cellulose, cross-linked sodium carboxymethyl cellulose, cross-linked hydroxypropyl cellulose), starch per se (such as sodium starch glycollate, pregelatinised starch, maize starch, potato starch, rice starch, wheat starch) and others (such as cross linked polyvinylpyrrolidone, cationic exchange resin).

The binder is selected from the group consisting of cellulose per se (such as sodium carboxymethylcellulose, hydroxypropyl cellulose, hydroxypropyl methylcellulose, methyl cellulose), polymers (such as polyvinylpyrrolidone, polyethylene glycol), gelatins (such as hydrolysed gelatin), and traditional binders (such as starch, natural gums).

The lubricant is selected from the group consisting of insoluble lubricants (such as magnesium stearate, calcium stearate, zinc stearate, stearic acid, oils, talc, sodium stearyl fumarate), and soluble lubricants (such as polyethylene glycol, sodium benzoate, sodium lauryl sulfate).

In the formulation according to the invention the different constituents are preferably included in the following proportions, calculated by per cent w/w of the finished tablet:

Thrombin inhibitor: 1–35%, preferably 1–15%.

Filler: 35–90%, preferably 45–80%, when microcrystalline cellulose 50–90%, preferably 60–80% and most preferably 72–76%, when nonswelling filler 0–50% when mannitol 0–15%, preferably 5–10%.

Disintegrant: 0–35%, preferably 7–35%, when sodium starch glycollate 3–20%, preferably 5–10%.

Binder: 0–15%, preferably 4–12%, when polyvinylpyrrolidone 3–15%, preferably 5–10%.

Lubricant: 0–5%, preferably 0.5–1.5%, when sodium stearyl fumarate 0.5–1.5%, preferably above 1%.

In the invention it was found that a formulation comprising the active component with a particle size less than 300 µm, preferably less than 150 µm and with a preferred mean particle size less than 80 µm, fillers (e.g. microcrystalline cellulose (50–90%, preferably 74%), mannitol (0–15%, preferably 8.5%) disintegrant (e.g. sodium starch glycollate 3–20%, preferably 8.5%), moistened with with a suitable binder (e.g. polyvinylpyrrolidone K 90 (3–15%, preferably 8%) and finally mixed with suitable lubricant (e.g: sodium stearyl fumarate (0.5–1.5%, preferably 1%) provided a tablet having good technical properties and a very small pH dependent dissolution.

The formulations according to the invention can preferably be prepared either by direct compression or by wet granulation technique.

Direct Compression

A low molecular weight thrombin inhibitor is mixed with the filler or fillers and if necessary the disintegrant. This mixture is then mixed with the lubricant and compressed to the tablets.

Wet Granulation

A low molecular weight thrombin inhibitor is mixed with the filler or fillers, and if necessary the disintegrant. The mixture is then moistened with a suitable solvent in which the binder may be dissolved. After drying the granulate is milled and then mixed with the lubricant and compressed to tablets

WORKING EXAMPLES

Example 1

Drug Dissolution from Tablets According to the Invention

IR tablets of the thrombin inhibitor, Compound A, were prepared by mixing Compound A microcrystalline cellulose, sodium starch glycollate and mannitol The mixture was moistured with a suitable amount of polyvinylpyrrolidone K 90 dissolved in water. After drying, the granulate was milled and then mixed with sodium stearyl fumarate and compressed to tablets.

|  | mg/tabl |
| --- | --- |
| Compound A | 24 |
| Microcrystalline cellulose (MCC pH 101) | 140 |
| Sodium starch glycollate | 16 |
| Mannitol | 16 |
| Polyvinylpyrrolidone K 90 | 15 |
| Water | q.s. |
| Sodium stearyl fumarate | 2 |
| Punches: | 9 mm |
| Tablet weight: | 213 mg |
| Hardness: | 110 N |

The obtained tablets were analyzed with regard to dissolution of Compound A using a USP dissolution apparatus No. 2 (paddle), 100 rpm, 500 ml. The dissolution medium used had a temperature of 37° C. Two different dissolution media were used, 0.1 M HCl pH 1 and phosphate buffer pH 6.8 (ionic strength 0.1). The amount of Compound A released was determined by UV-spectrometry.

Results are shown in FIG. 1. After 30 minutes the amount of Compound A dissolved was 94% (average n=3) in 0.1 M HCl and 94% (average n=3) in phosphate buffer pH 6.8.

Example 1b

Drug Dissolution from Tablets According to the Invention

IR tablets of thrombin inhibitor, Compound A were prepared by mixing Compound A, microcrystalline cellulose and maize starch and the mixture was moistured with a suitable amount of maize starch (paste). After drying the granulate was milled and then mixed with polyvinylpyrrolidone crosslinked. Finally the sodium stearyl fumarate was admixed and the granulate was compressed into tablets.

|  | mg/tabl |
| --- | --- |
| Compound A | 30 |
| Microcrystalline cellulose | 115 |
| Maize starch | 55 |
| Maize starch (paste) | 6 |
| Water | q.s. |
| Polyvinylpyrrolidone crosslinked | 10 |
| Sodium stearyl fumarate | 2.2 |
| Punches: | 8.5 mm |
| Tablet weight: | 219 mg |
| Hardness: | 110 N |

The obtained tablets were analysed for dissolution of Compound A according to the method described in Example 1. Results are shown in FIG. 2. After 30 minutes the amount of Compound A dissolved was 100% (average n=3) in 0.1 M HCl and 97% (average n=3) in phosphate buffer pH 6.8.

Example 2

Drug Dissolution from Tablets According to the Reference

Lachman (The theory and practice of industrial pharmacy 1986, 343, appA) describes another composition and manufacturing of a "standard" granulate for an IR tablet. IR tablets of the thrombin inhibitor, Compound A, were prepared according to this method by mixing Compound A, tricalcium phosphate and the mixture was moistened with pre-gelatinated maize starch dissolved in water. After drying the granulate was milled and then mixed with talc Finally, the mineral oil was admixed and the granulate was compressed to tablets.

| | | |
|---|---|---|
| Compound A | 24 | |
| Tricalcium phosphate | 100 | |
| Pregelatinized starch | 15 | |
| Water | q.s. | |
| Talc | 60 | |
| Mineral oil, light | 4 | |
| Punches: | 9 | mm |
| Tablet weight: | 198 | mg |
| Hardness: | 12 | N |

The obtained tablets were analysed for dissolution of Compound A according to the method described in Example 1. Results are shown in FIG. 2. After 30 minutes the amount of Compound A dissolved was 40% (average n=3) in 0.1 M HCl and 5% (average n=3) in phosphate buffer pH 6.8.

Example 3

Drug Dissolution from Tablets According to the Reference

Lachman (The theory and practice of industrial pharmacy 1986,343, appA) describes composition and manufacturing of another "standard" granulate for an IR tablet. IR tablets of thrombin inhibitor, Compound A were prepared according to this method by mixing Compound A and lactose and the mixture was moistened with starch dissolved in water.

After drying the granulate was milled and then mixed with dry starch and talc. Finally the mineral oil was admixed and the granulate was compressed to tablets.

| | | |
|---|---|---|
| Compound A | 24 | |
| Lactose | 110 | |
| Starch (paste) | 5 | |
| Starch | 28 | |
| Talc | 28 | |
| Mineral oil 50 cps | 11 | |
| Punches: | 9 | mm |
| Tablet weight | 206 | mg |
| Hardness: | 13 | N |

The obtained tablets were analysed for dissolution of Compound A according to the method described in Example 1. Results are shown in FIG. 3. After 30 minutes the amount of Compound A dissolved was 100% (average n=3) in 0.1 M HCl and 74% (average n=3) in phosphate buffer pH 6.8.

SHORT DESCRIPTION OF THE FIGURES

FIG. 1: Dissolution of the thrombin inhibitor Compound A from tablets according to the invention as described in Example 1. (No figure is given for example 1b).

FIG. 2: Dissolution of the thrombin inhibitor Compound A from tablets according to the reference as described in Example 2

FIG. 3: Dissolution of the thrombin inhibitor Compound A from tablets according to the reference as described in Example 3

CONCLUSION (EXAMPLES)

From the Examples it is obvious that a sufficient quality of the product is not achieved when using a "standard" granulate. Either the technical properties are bad [Example 2 and 3,] and/or the dissolution in phosphate buffer pH 6.8 does not meet the definition of a rapidly dissolving drug product in Guidance for Industry. Waiver of in Vivo Bioavailability and Bioequivalens Studies for Immediate Release Solids Dosage Forms Containing Certain Active Moieties/Active Ingredients Based on Biopharmaceutics Classification System. With the formulation according to the invention the dissolution is fast in both media and the technical properties are excellent.

What is claimed is:

1. A method for the treatment of thromboembolism comprising administering, to a mammal in need thereof, a therapeutically effective amount of an oral immediate release formulation in solid form, wherein the oral formulation comprises (a) a low molecular weight peptide thrombin inhibitor having pH dependent solubility and having a particle size of less than 300 μm, and (b) a combination of microcrystalline cellulose and sodium starch glycollate in an amount higher than 35% w/w of the formulation.

2. The method according to claim 1, wherein the low molecular weight peptide thrombin inhibitor is selected from the group consisting of inogatran, melagatran and (glycine, N-[1-cyclohexyl-2-[2-[[[[4-[(hydroxyimino)aminomethyl]-phenyl]methyl]amino]carbonyl]-1-azetidinyl]-2-oxoethyl]-, ethyl ester, [S-(R*, S*)]-).

3. The method according to claim 1, wherein the low molecular weight peptide thrombin inhibitor is (glycine, N-[1-cyclohexyl-2-[2-[[[[4-[(hydroxyimino)aminomethyl]-phenyl]methyl]amino]carbonyl]-1-azetidinyl]-2-oxoethyl]-ethyl ester, [S-(R*, S*)]-).

4. The method according to claim 1, wherein the thrombin inhibitor has a particle size of less than 150 μm.

5. The method according to claim 1, wherein the thrombin inhibitor has a mean particle size less than 80 μm.

6. The method of claim 1, wherein the thrombin inhibitor constitutes 1–35% (w/w) of the formulation.

7. The method according to claim 1, wherein the microcrystalline cellulose constitutes 50–90% (w/w) of the formulation.

8. The method according to claim 1, wherein sodium starch glycollate constitutes 3–20% (w/w) of the formulation.

9. The method according to claim 1, wherein the oral formulation further comprises one or more components selected from the group consisting of a sugar, a disintegrant, a binder and a lubricant.

10. The method according to claim 9, wherein the sugar constitutes up to 15% (w/w) of the oral formulation.

11. The method according to claim 9, wherein the sugar is mannitol.

12. The method according to claim 9, wherein the binder is constitutes up to 15% (w/w) of the formulation.

13. The method according to claim 9, wherein the binder is a polyvinylpyrrolidone.

14. The method according to claim 1 or 9, wherein the oral formulation comprises:

a thrombin inhibitor 1–35% (w/w);

microcrystalline cellulose 50–90% (w/w);

sodium starch glycollate 3–20(w/w);

mannitol 0–15% (w/w);

polyvinylpyrrolidone K 90 3–15% (w/w); and, sodium stearyl fumarate 0.5–1.5% (w/w).

15. A method for inhibiting thrombin in a mammal, comprising administering to said mammal a therapeutically effective amount of an oral immediate release formulation in solid form, wherein the oral formulation comprises (a) a low molecular weight peptide thrombin inhibitor having pH dependent solubility and having a particle size of less than 300 µm, and (b) a combination of microcrystalline cellulose and sodium starch glycollate in an amount higher than 35% w/w of the formulation.

16. The method according to claim 15, wherein the low molecular weight peptide thrombin inhibitor is selected from the group consisting of inogatran, melagatran and (glycine, N-[1-cyclohexyl-2-[2-[[[[4-[(hydroxyimino)aminomethyl]-phenyl]methyl]amino]carbonyl]-1-azetidinyl]-2-oxoethyl]-, ethyl ester, [S-(R*, S*)]-).

17. The method according to claim 15, wherein the low molecular weight peptide thrombin inhibitor is (glycine, N-[1-cyclohexyl-2-[2-[[[[4-[(hydroxyimino)aminomethyl]-phenyl]methyl]amino]carbonyl]-1-azetidinyl]-2-oxoethyl]-, ethyl ester, [S-(R*, S*)]-).

18. The method according to claim 15, wherein the thrombin inhibitor has a particle size of less than 150 µm.

19. The method according to claim 15, wherein the thrombin inhibitor has a mean particle size less than 80 µm.

20. The method of claim 15, wherein the thrombin inhibitor constitutes 1–35% (w/w) of the formulation.

21. The method according to claim 15, wherein the microcrystalline cellulose constitutes 50–90% (w/w) of the formulation.

22. The method according to claim 15, wherein sodium starch glycollate constitutes 3–20% (w/w) of the formulation.

23. The method according to claim 15, wherein the oral formulation further comprises one or more components selected from the group consisting of a sugar, a disintegrant, a binder and a lubricant.

24. The method according to claim 23, wherein the sugar constitutes up to 15% (w/w) of the oral formulation.

25. The method according to claim 23, wherein the sugar is mannitol.

26. The method according to claim 23, wherein the binder is constitutes up to 15% (w/w) of the formulation.

27. The method according to claim 23, wherein the binder is a polyvinylpyrrolidone.

28. The method according to claim 15 or 23, wherein the oral formulation comprises:

a thrombin inhibitor 1–35% (w/w);

microcrystalline cellulose 50–90% (w/w);

sodium starch glycollate 3–20% (w/w);

mannitol 0–15% (w/w);

polyvinylpyrrolidone K 90 3–15% (w/w); and, sodium stearyl fumarate 0.5–1.5% (w/w).

* * * * *